United States Patent [19]

Kisilevsky

[11] Patent Number: 5,318,958
[45] Date of Patent: Jun. 7, 1994

[54] AMYLOID PRECURSOR PROTEIN

[75] Inventor: Robert Kisilevsky, Kingston, Canada

[73] Assignee: Queen's University at Kingston, Ontario, Canada

[21] Appl. No.: 890,936

[22] Filed: May 29, 1992

[51] Int. Cl.$^5$ .................... A61K 37/02; A61K 37/22
[52] U.S. Cl. ......................................... 514/21; 514/2; 514/12
[58] Field of Search ............................... 514/2, 12, 21

[56] References Cited

PUBLICATIONS

Kisilevsky et al. Laboratory Investigation, vol. 66, No. 6, pp. 778-785, 1992.
Feussner et al. Electrophoresis, vol. 12 (4), pp. 283-286, 1991.
Cabana et al. J. Lipid Res., vol. 30, pp. 39-49, 1989.
Sipe et al. "Amyloid & Amyloidosis", International Symp. on Amyl., 1990, pp. 57-61.
Steinmetz et al. Bioch. Biophy. Acta, vol. 1006, pp. 173-178, (1989).
Glomset J. of Lipid Res., vol. 9, No. 2, pp. 155-167, 1968.

Primary Examiner—Michael G. Wityshyn
Assistant Examiner—Choon Koh
Attorney, Agent, or Firm—Reising, Ethington, Barnard, Perry & Milton

[57] ABSTRACT

A method is provided for potentiating the efflux of cholesterol from the macrophage, the method including the steps of increasing the affinity of high-density lipoprotein for macrophages by the administration of a serum amyloid A/high-density lipoprotein complex, exposing the macrophage to the complex, and potentiating macrophage cholesterol efflux.

4 Claims, 4 Drawing Sheets

AMYLOID PRECURSOR PROTEIN

TECHNICAL FIELD

The present invention relates to means for potentiating the collection of cholesterol from inflammatory or atherosclerotic sites, having the capability of being used to treat hypercholesterolemia and improving atherosclerotic conditions. More specifically, the present invention provides a therapeutic method which potentiates the ability to transfer macrophage cholesterol to a natural transport mechanism for subsequent excretion.

BACKGROUND OF THE INVENTION

Serum levels of cholesterol and atherosclerosis are significant topics addressed by health care professionals as they relate to cardiac disease, as well as other circulatory and systemic diseases. There is a great interest in the medical field with regard to the reduction of serum cholesterol and the reversal of an atherosclerotic condition.

Various means have been used in an attempt to lower serum cholesterol. For example, various resins have been administered therapeutically to sequester bile acids and thereby reduce systemic cholesterol levels. Other therapeutics have been administered in an attempt to effect cholesterol metabolism. However, there remains a high level of interest and need for more effective therapeutics in this area.

Serum amyloid A (SAA) is an apolipoprotein which is present on high density lipoprotein (HDL) only during inflammatory states. SAA was discovered approximately 15 years ago in the course of studies examining serum for potential precursors to the inflammation-associated AA form of amyloid. It has been determined that the AA peptide responsible for the inflammation-associated amyloid fibril represented a fragment of the SAA protein (1,2). Based on amino acid sequencing of SAA in the preparation, cloning, and identification of genes possessing the information for this protein (1,3), it became apparent that SAA was not a single protein, but rather a family of several related proteins. Work with these proteins have shown that during an inflammatory reaction, the cytokines interleukin-1, interleukin-6 and tumor necrosis factor are responsible for regulating the transcription of the SAA gene in liver (4,5). Recent studies have suggested that SAA has a significant influence on lecithin cholesterol acyl transferase activity associated with the HDL (6).

It is well established that SAA is present in the circulation in substantial quantities only during inflammation. Ninety percent (90%) or more of the SAA is associated with HDL's. HDL is also well established in the function of reverse cholesterol transport (7).

With specific regard to atherosclerosis, observations in the early twentieth century in patients who had long standing infections or malignancies showed that these patients at the time of death had far less atherosclerosis, or had the equivalent of "healed" atherosclerosis, when compared to patients of equivalent age who did not have these preceding disorders. This observation was always attributed to the patient's debilitated physical state or that their nutritional state was inadequate when compared to healthy individuals of the same age.

Based on the above compiled observations, and based on studies observing the potential roles of SAA's as a signal to HDL's, the present invention provides means for potentiating the efflux of macrophage cholesterol, thereby providing a means for therapeutically reducing cholesterol at atherosclerotic sites. This potentiating effect should lead to reversal of an atherosclerotic condition.

SUMMARY OF THE INVENTION

In accordance with the present invention, there is provided a method of potentiating the collection of macrophage cholesterol by increasing the affinity of high-density lipoprotein for macrophages, exposing the macrophage to the HDL, and potentiating the release of macrophage cholesterol to the natural system which eventually excretes cholesterol.

BRIEF DESCRIPTION OF THE FIGURES

Other advantages of the present invention will be readily appreciated as the same becomes better understood by reference to the following detailed description when considered in connection with the accompanying drawings wherein.

DETAILED DESCRIPTION OF THE INVENTION

Generally, the present invention provides a method of potentiating the collection of macrophage cholesterol by increasing the affinity of high-density lipoprotein for macrophages, exposing the macrophage to HDL, and potentiating the release of macrophage cholesterol to the reverse cholesterol transport mechanism. Although the role of HDL in the physiology of macrophage capacity to carry has been studied, the present invention provides the initial discovery of the ability to alter and significantly increase the affinity of HDL for the macrophage. This increase affinity is biochemically directly related to increased capacity of HDL to collect macrophage cholesterol for subsequent excretion.

More specifically, the affinity of HDL for macrophages is increased by binding serum amyloid-A (SAA) or a ligand having serum SAA binding activity to HDL. This can be accomplished by binding native SAA to HDL or by binding a ligand having SAA affinity binding to the HDL. Such a ligand can be derived by isolating the active site of SAA on HDL binding, SAA having been sequenced, CDNA being derived, and the genes being cloned. Similarly, the active site on SAA for macrophage binding may be determined. Hence, state of the art modeling to derive the active site would result in derivation of a ligand having SAA activity. This would be advantageous since it is known that administration of SAA per se could possibly lead to undesirable amyloid formation as a side effect.

Administration of the SAA/HDL complex can be accomplished by various means, such as infusion of a solution including the SAA/HDL complex so as to provide an amount of the complex systemically to effectively induce macrophage cholesterol efflux.

Preparation of SAA/HDL complexes use standard methodologies (see references 9 and 10). Isolation of SAA also uses standard methodologies (see references 1 and 10).

The following experimental data demonstrates the capacity of HDL/SAA administration to significantly shift the HDL cholesterol carrying capacity towards the macrophage. The data specifically demonstrates the effect of SAA to reduce HDL's affinity for normal hepatocytes by a factor of 2. In contrast, the HDL/SAA complex had a 3 to 4 fold higher affinity for macrophages then HDL alone. A profound effect on this finding is the further finding that the number of binding sites for HDL/SAA increased on macrophages during inflammation, while decreasing on hepatocytes. The data further provides competition experiments showing that there is a specific SAA binding site on macrophages. Hence, it can be concluded from the factual evidence that SAA provides a specific directionality for HDL towards macrophages, the macrophages thereby having an increased capacity of the reverse cholesterol transport mechanism with which to release cholesterol. The net result is a redistribution or excretion of cholesterol from atherosclerosis sites which can result in a therapeutic effect. Thus, there is a use for such a therapeutic in the treatment of atherosclerosis, and also as an adjunct to other cholesterol lowering therapies. Further, the following experiments provide means for demonstrating the patient's HDL effectiveness as a potentiator in combination with the SAA for potentiating the efflux of macrophage cholesterol to the mechanism which transports cholesterol to its natural site for excretion.

SUPPORTING EXPERIMENTS

The following experiments were designed to test whether SAA bound to HDL altered HDL's affinity for specific cells. Further tests were conducted to determine whether cells collected at different times during an inflammatory reaction in turn change in their interactions with HDL or HDL/SAA. Additional experiments demonstrate that the above differences were occurring predominantly through the effect of the SAA protein of the ligand as opposed to the apoA-1.

Binding studies were conducted between various concentrations of HDL, HDL/SAA, and fixed numbers of normal hepatocytes or peritoneal macrophages. Similar binding studies were also conducted with hepatocytes and macrophages obtained at several time points after the induction of inflammation. Binding curves were constructed between macrophages or hepatocytes in different physiological states and various concentrations of HDL or HDL/SAA.

Finally, competition binding studies were conducted between $^{125}$I-HDL, and unlabelled HDL or HDL/SAA for macrophages, and conversely between $^{125}$I-HDL/SAA and unlabelled HDL or HDL/SAA for macrophages. These experiments determined if apoA-1 (the presumed ligand from macrophages HDL binding sites) or the SAA content of the competitor correlated with the inhibition of binding.

Materials and Methods

Collagenase (Type 1) and fatty acid free bovine serum albumin (BSA) were purchased from Sigma Chemical Company, St. Louis, Mo., and iodine monochloride from Aldridge Chemical Company, Milwaukee, Wis. Dibutyl phthalate (d=1.046) and dinonyl phthalate (d=0.97) were obtained from Fluka Chemical Corporation, New York, N.Y. Nitex nylon membrane filters were purchased from B & SH Thompson Company Limited, Ville Mont Royale, Quebec. William's medium and RPMI medium were bought from Gibco Incorporated, Grand Island, N.Y.

Animals

All mice were of the CD/1 strain and 6–8 weeks old, purchased from Charles Rivers, Montreal, Quebec. Some animals were treated with a subcutaneous injection of 0.5 ml of 2% $AgNO_3$ to produce a sterile subcutaneous inflammatory reaction as described previously (8).

Preparation of Cells

Hepatocytes. Hepatocytes were isolated from 6–8 week old CD/1 mice by liver perfusion. The cells were collected in William's medium which had been pregassed with 95% $O_2$ and 5% $CO_2$ for 15 minutes, washed twice in William's medium and centrifuged for five minutes at room temperature at 150×g. The cells were resuspended in William's medium containing 5 mM HEPES and 2% BSA, counted, and diluted to a concentration of $6 \times 10^6$ cells/ml. They were kept on ice 0°–4° C. for ligand binding studies. Hepatocytes were also collected from mice 24 and 72 hours after subcutaneous injections of $AgNO_3$.

Peritoneal Macrophages

Peritoneal macrophages were collected either from normal mice or mice treated with $AgNO_3$ as described above. The mice were sacrificed by cervical dislocation, the peritoneal cavity filled with 5 ml of cold RPMI 1640 medium containing 0.5% BSA and massaged gently by hand. The peritoneal wash containing macrophages was withdrawn with the same syringe and filtered through a Nitex filter (100 $\mu$) into a 50 ml centrifuge tube kept in an ice bath. Washings from 10–12 mice were collected in each tube, centrifuged twice at 300×g for 10 minutes and resuspended in cold RPMI 1640 containing 5 mM HEPES and 2% BSA. Following a cell count, the concentration was adjusted to the desired cell concentration and the diluted suspension kept cold before use in ligand binding experiments.

Preparation of Lipoproteins

Under anesthesia (sodium nembutal 6 mg/kg), mice were exsanguinated from the retroorbital sinus into a small quantity of EDTA which was used as an anticoagulant. Following centrifugation to remove the cells an HDL fraction was prepared from the EDTA treated plasma of normal mice, and those receiving the $AgNO_3$ 24 hours earlier. These plasma samples were fractionated by floatation in KBr (9, 10). After removing the low density lipoprotein (density 1.006–1.063), HDL and HDL/SAA were collected from the top layers of plasma whose density was adjusted to 1.21 with KBr. The collected lipoprotein was overlayed with KBr (density+1.21) and recentrifuged. The washed sample was dialysed for 24 hours against EDTA saline (10 mM EDTA). The protein content was determined by the standard Lowry techniques (11).

Labelling Procedure

High density lipoprotein was iodinated with Na$^{135}$I using the iodine monochloride method, and purified by ion exchange chromatography. Iodination was done at pH 10, and greater than 95% of the radioactivity was found to be protein bound. On electrophoresis in 12% polyacrylamide gels containing 0.1% SDS and beta mercaptoethanel, followed by autoradiography, only $^{125}$I-apoA-I and $^{125}$I-apoA-II were detectable in the HDL preparations, while apoA-1, SAA, and apoE were detected in the HDL/SAA preparations. In HDL, more than 95% of the protein was represented by apoA-1, while in the HDL/SAA preparations approximately equal quantities of apoA-I and SAA were detected.

Binding Experiments

All binding experiments were performed at 4° C. Both the cells and ligand were kept on ice for at least 30 minutes prior to the experiment. William's medium containing 5 mM HEPES and 2% BSA were used as the medium both for the cells and ligand dilutions. Appropriate concentrations of labelled ligand (final concentrations 0.1-55 μg/ml) were added to known cell concentrations ($5 \times 10^5 - 1 \times 10^6$ cells/ml) in a polypropylene tube (final volume 0.5 ml) which was then tightly closed and incubated for two hours at 4° C. while constantly being mixed on a rotator. The cells were washed free of unbound label by centrifuging a known volumed of cell suspension through a layer of equal volumes of medium and phthalate mixture, in a conical microvial in a microfuge. The supernatant containing the incubation medium and the separating oil were removed by aspiration and the remaining liquid was drained. The tip of the microvial, with the cell pellet, was removed with a razor blade and the radioactive counts determined in a gamma counter (Beckman Gamma 550B) with an appropriate background subtraction.

Quantitative Analysis of Binding Data

The binding data were analysed as described in detail previously (12). It was assumed that thermodynamic equilibrium for the formation of a ligand and its binding site, and a polynomial was constructed based on a single class of sites where the experimentally measured quantity $B_{exp}$ was a function of the concentration of ligand [L].

$$B_{exp} = B_o + s \times [L] + \frac{B_{max} \times [L]}{[L] + K_d}$$

where $B_o$ is the background in the absence of added ligand;
s is the proportionality constant for nonspecific binding;
and Bmax is the total binding capacity.

Additional terms were added when analysing the data for two classes binding sites, or exponential terms for cooperative binding.

Figure 2A:
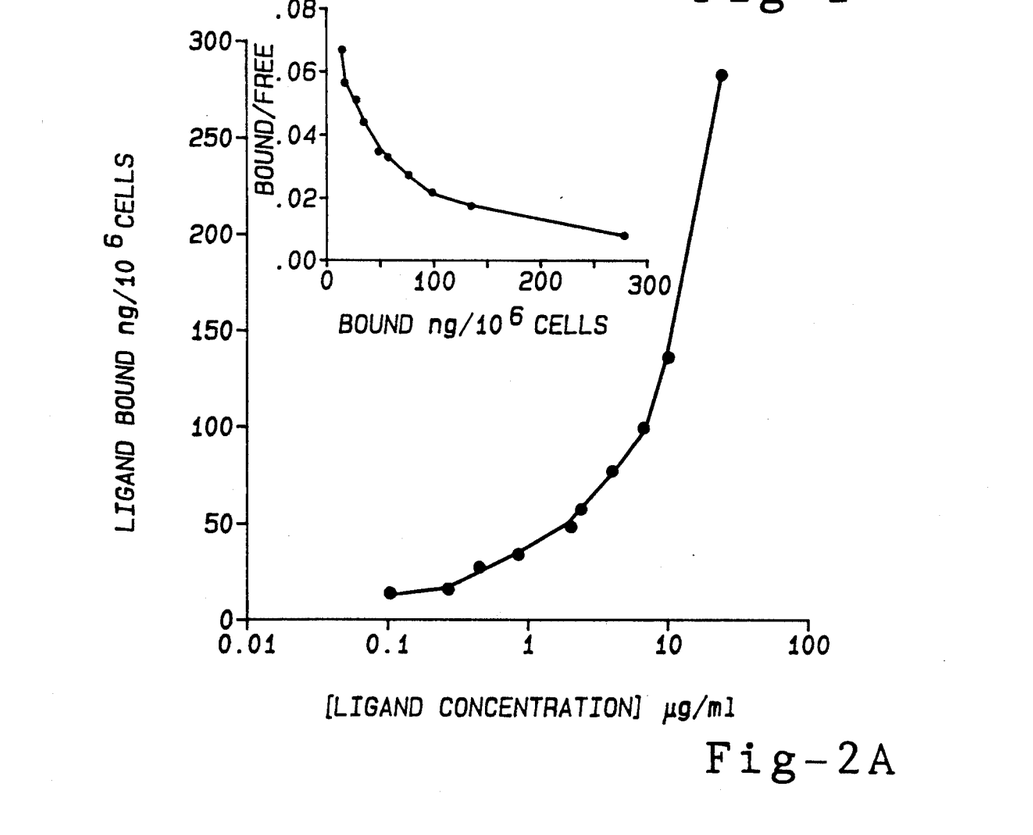
FIGS. 2A & 2B show saturation binding curves of HDL (panel A) and HDL/SAA (panel B) for hepatocytes from various physiological conditions.
Figure 2B:
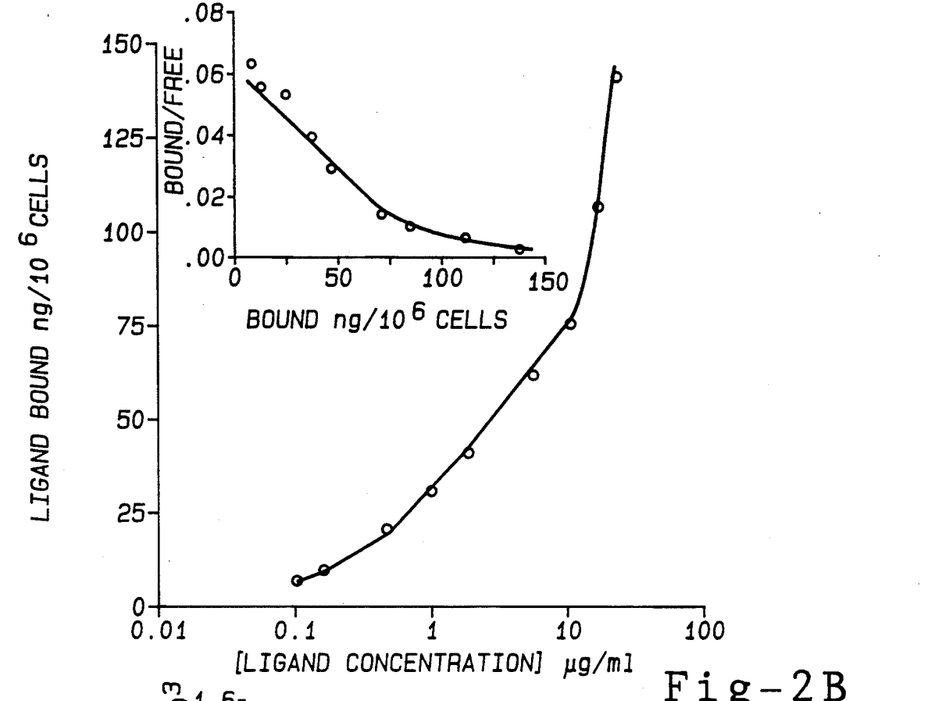
Figure 3A:
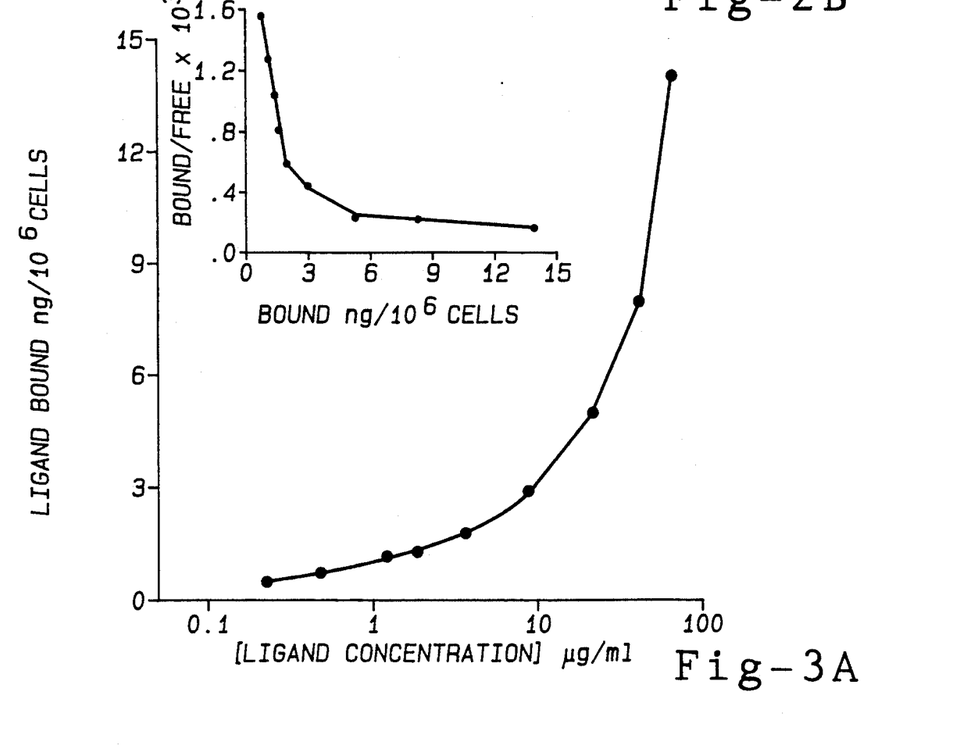
FIGS. 3A & 3B show saturating binding curves of a HDL (panel A) and HDL/SAA (panel B) for peritoneal macrophages from various physiological conditions, the individual points representing the experimental data and the solid lines representing the curves of best fit, which provided the values of the parameters set forth in the result sections, the insets representing Scatchard plots.
Figure 3B:
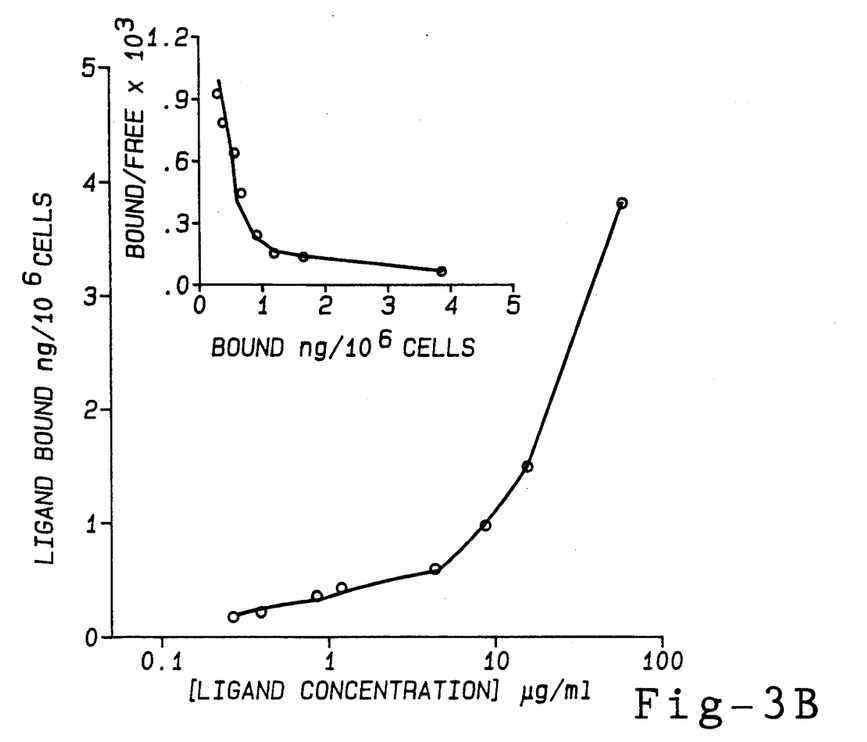

Accordingly, the $B_{exp}$ vs [L] were analysed using an objective non-linear curve fitting program (Sigma Plot 4.0, Jandel Scientific). Representative curves and the values of the parameters are illustrated in FIGS. 2 and 3. FIG. 2 shows saturation binding curves of HDL (panel A) and HDL/SAA (panel B) for hepatocytes from various physiological conditions. Log plots of ligand concentrations have been used to better illustrate binding at low concentrations. The individual points represent the experimental data. The solid lines represent the curves of best fit employing the polynomial for a single class of binding sites described above. The parameters were obtained from the curves of best fit. The insets represent Scatchard plots. Each such experiment was performed in triplicate. The spread of results and their statistical analyses are presented in Table 1.

Panel A: A representative curve of HDL binding to normal hepatocytes
Values of parameters are: $B_o = 3$ ng; $S = 6.3 \times 10^{-3}$ ml; $B_{max} = 84.8$ ng; $K_d = 2.19$ μg/ml Panel B: A representative curve of HDL/SAA binding to hepatocytes 72 hours after inducing inflammation
Values of parameters are: $B_o = 0.1$ ng; $S = 1.3 \times 10^{-3}$ ml; $B_{max} = 77.2$ ng; $K_d = 1.30$ μg/ml FIG. 3 shows saturation binding curves of HDL (panel A) and HDL/SAA (panel B) for peritoneal macrophages from various physiological conditions. The individual points represent the experimental data. The solid lines represent the curves of best fit, which provided the values of the parameters listed below. The insets represent Scatchard plots. Each such experiment was performed in triplicate. The spread of results and their statistical analyses are presented in Table 2.

Panel A: A representative curve of HDL binding to normal macrophages
Values of parameters are: $B_o 3.2 \times 10^{-2}$ ng; $S = 0.15 \times 10^{-3}$ ml; $B_{max} = 2.1$ ng; $K_d = 1.4$ μg/ml Panel B: A representative curve of HDL/SAA binding to normal macrophages
Values of parameters are: $B_o = 3.4 \times 10^{-9}$ ng; $S = 0.08 \times 10^{-3}$ ml; $B_{max} = 0.6$ ng; $K_d = 0.37$ μg/ml More complex binding models gave no better curve fits than a single class of binding sites. Scatchard plots have been inserted for completeness, not for the calculation of the parameters which were obtained from the curves of best fit.

DISCUSSION OF EXPERIMENTAL DATA

Equilibrium Binding of HDL or HDL/SAA

Figure 1:
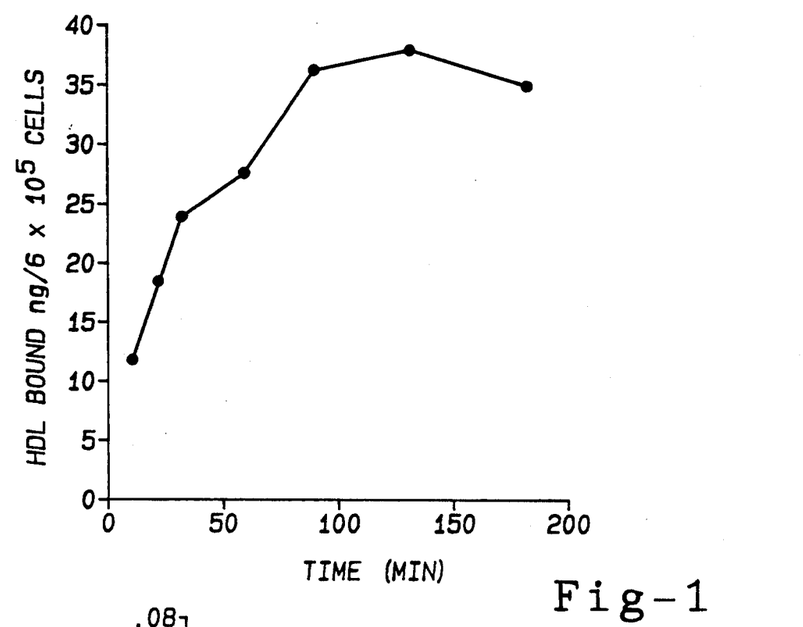
FIG. 1 shows a representative binding curve of $^{125}$I-HDL (10 µg/ml) to normal hepatocytes as a function of time.

The binding of the ligands (HDL/SAA) to cells (hepatocytes or macrophages) was initially done as a function of time to determine the time needed for the labelled ligand to reach maximum equilibrium binding. The labelled ligand, at a concentration of 10 μg/ml was added to either macrophages or hepatocytes ($6 \times 10^6$/ml) which had been precooled on ice. The ligand and cell suspension were incubated for three hours, mixing constantly in a rotator. Aliquots of the cell suspension (100 μl) were taken at different time points and the cells and attached ligand pelleted through oil as described above. The amount of ligand bound at each time interval was determined from the radioactive counts and knowledge of the specific activity of ligand. FIG. 1 demonstrates a representative binding curve of $^{125}$I-HDL to mouse hepatocytes over a period of three hours. Similar results were obtained for HDL/SAA. These experiments were repeated on at least three occasions using separate preparations of cells and ligand. An equilibrium state of binding was reached within 90 minutes. Peritoneal macrophages gave very similar results. A binding time of two hours was therefore used in all subsequent experiments. To demonstrate the specificity of binding, competition experiments in the presence of a hundred fold excess unlabelled ligand prevented the binding of its corresponding labelled partner (data not shown). Competition binding studies between labelled HDL and "cold" HDL/SAA and the converse, were also applied.

Saturation Binding Curves

Representative examples of saturation binding curves of hepatocytes for varying concentrations of HDL, and for varying concentrations of HDL/SAA are shown in FIGS. 2A and 2B respectively. Scatchard plots of these data are presented as the insets in FIGS. 2A and 2B.

The individual points in FIG. 2 represent the actual experimental data. The solid lines represent the curve of best fit as obtained from the curve fitting program and the single binding site polynomial described above. Similar binding curves of HDL and HDL/SAA for peritoneal macrophages are shown in FIGS. 3A and 3B respectively.

The dissociation constants (Kd's) and the maximum binding of the ligand ($B_{max}$) were obtained from the best fit parameters, using the aforementioned mathematical formulation as set forth above.

Each of the above experiments were performed in triplicate. A summary and statistical analysis of the Kd's and the $B_{max}$ from the binding studies of HDL and HDL/SAA for hepatocytes from various physiological settings is presented in Table 1. It is apparent that with normal hepatocytes, HDL has an affinity twice as high as HDL/SAA. Twenty-four hours into an inflammatory state, the affinity of HDL for hepatocytes decreased by a factor of 2, but by 72 hours it has returned to a pre-inflammatory level. This result with HDL and hepatocytes probably reflects the large quantity of SAA synthesis and secretion by hepatocytes which occurs in vivo 24 hours following the induction of inflammation (13). However, it is only the SAA on the surface of the hepatocytes which may complicate the interpretation of the results. Such hepatocyte HDL/SAA on the cell surface may occupy binding sites and allow exogenously added HDL, or HDL/SAA to bind only to unoccupied sites. This would lead to an underestimate of the $B_{max}$ but not alter the Kd's. Any secreted HDL/SAA would compete with exogenous ligand and lead to an underestimate of both parameters. Since all binding studies were done at 0° C., the latter possibility is minimized. These considerations would be less of a problem at the 72 hour interval when HDL/SAA levels drop significantly.

HDL/SAA's affinity for hepatocytes continued to increase with time. The Kd dropped from 32 nM to 17 nM and 6 nM (assuming an average molecular weight of HDL/SAA of 175 kDa) at 24 and 72 hours respectively. A physiologic change is probably taking place in the hepatocyte during inflammation increasing its affinity for HDL/SAA. A potential mechanism involving apolipoprotein E (apoE) is presented below. The hepatocyte $B_{max}$ for HDL did not increase at 24 hours but was two fold higher at 72 hours. In contrast, with HDL/SAA there was relatively little change in $B_{max}$ at 24 hours but a significant drop occurred at 72 hours.

Table 2 contains a summary and statistical analysis of the Kd's and $B_{max}$ for HDL's and HDL/SAA's interaction with peritoneal macrophages. The affinity of HDL/SAA for normal macrophages was three to four fold higher than HDL alone. Twenty-four and 72 hours into an inflammatory reaction, there was no change in HDL's affinity or $B_{max}$ for HDL. Here again there may be an underestimate of the $B_{max}$ at the 24 hour interval as the macrophages are harvested from animals with a high level of SAA. The extent to which endogenous SAA would be a confounding problem in the macrophage binding studies would be far less important than with hepatocytes, since it has been shown that peritoneal macrophages contain little SAA even during inflammation (14). HDL/SAA consistently had a higher affinity for macrophages than HDL, regardless of time period into the inflammatory reaction at which one examined the macrophages.

It is possible to roughly calculate the number of binding sites per hepatocyte and macrophage from the experimentally determined $B_{max}$ values for $10^6$ cells. Knowing the number of ng of ligand bound per $10^6$ cells, the molecular weights of apoA-1 and SAA and the changing composition of apoA-1 and SAA on HDL 24 hours following the induction of inflammation (from essentially 100% apoA-1, molecular weight 27 kDa to approximately 50% apoA-1, 50% SAA, molecular weight 12 kDa), the HDL binding sites on macrophages remain relatively constant during inflammation at 30,000-35,000/cell. The HDL/SAA binding sites on macrophages increase significantly from 25,000 to 55,000/cell. With hepatocytes the corresponding figures are: for HDL, an increase from 160,000 to 325,000, and for HDL/SAA, a decrease from 400,000 to 95,000. The net effect of both the changes in affinity and numbers of binding sites is a significant shift in HDL cholesterol carrying capacity towards the macrophage.

HDL and HDL/SAA Competition Binding to Normal Macrophages

As demonstrated in the time course experiments, the presence of cold ligand at very high concentration essentially blocked the binding of its radiolabelled counterpart.

Figure 4A:
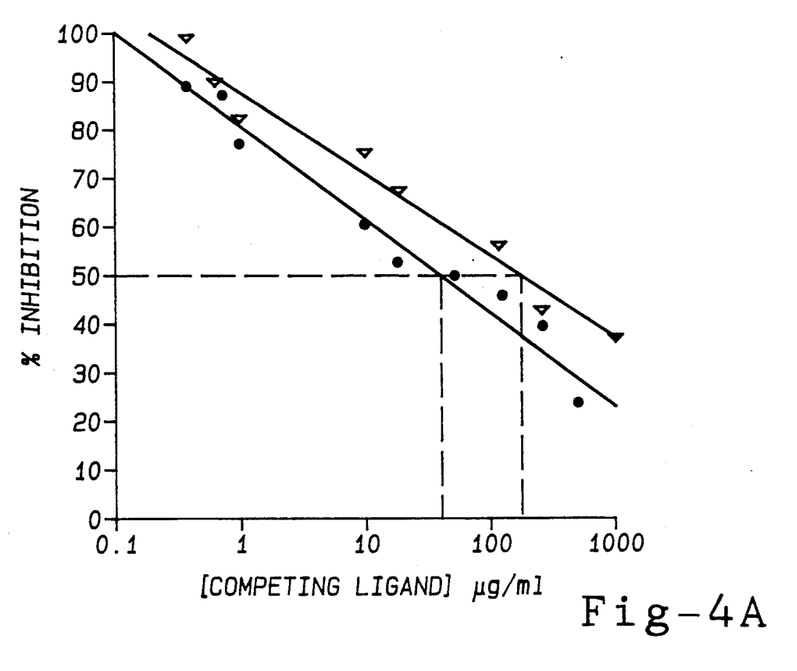
FIG. 4A shows the inhibition of $^{125}$I-HDL binding (10 µg/ml) to macrophages by increasing concentrations of its unlabelled counterpart (filled circles), or unlabelled HDL/SAA (open triangles)
Figure 4B:
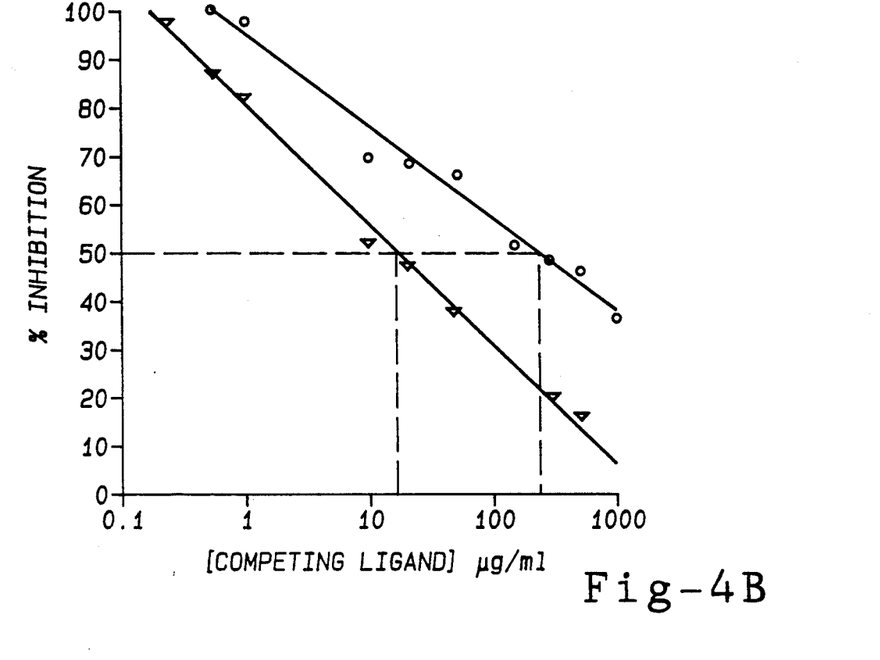
FIG. 4B shows the inhibition of $^{125}$I-HDL binding (10 µg/ml) to macrophages by increasing concentrations of its unlabelled counterpart (open triangles), or unlabelled HDL (filled circles)

To demonstrate both the specificity of binding as well as to examine whether the protein composition of the HDL/SAA or HDL had any influence on the binding of its labelled counterpart, a series of cross incubations were conducted using different concentrations of the unlabelled ligand. The object was to determine the concentration of unlabelled ligand required to produce a 50% reduction in the binding of labelled ligand. These data are shown in FIG. 4 and Table 3.

When using 10 μg/ml of $^{125}$I-HDL, the binding is reduced by approximately 50% with a concentration of approximately 45 μg/ml of "cold" ligand. In contrast, twice as much HDL/SAA is required to achieve an equivalent reduction in the binding of radiolabelled HDL to the same number of macrophages. This is in keeping with the known displacement of approximately half the apoA-1 by an equivalent amount of SAA, and the postulated interaction of HDL and macrophages through an apoA-1 receptor (15, 16, 17).

When using $^{125}$I-HDL/SAA at 10 μg/ml, approximately 25 μg/ml, unlabelled HDL/SAA were required to reduce the binding of the labelled counterpart by 50%. HDL has a higher apoA-1 content then HDL/SAA. If HDL/SAA was also binding to macrophages solely through apoA-1, then one would expect less unlabelled HDL, than HDL/SAA, to be effective in reducing labelled HDL/SAA binding by 50%. However, HDL was far less effective a competition than HDL/SAA. To achieve a 50% reduction of HDL/SAA binding, approximately 200 µg/ml HDL were required.

These results demonstrate two features. Firstly, the binding of HDL/AA and HDL to macrophages are specific phenomena. Secondly, the binding of HDL/SAA to macrophages probably occurs through binding sites which do not involve apoA-1.

When placed in the context of HDL function and the process of inflammation our results suggest a novel interpretation of SAA and HDL function in relation to cholesterol metabolism during inflammation.

Figure 5:
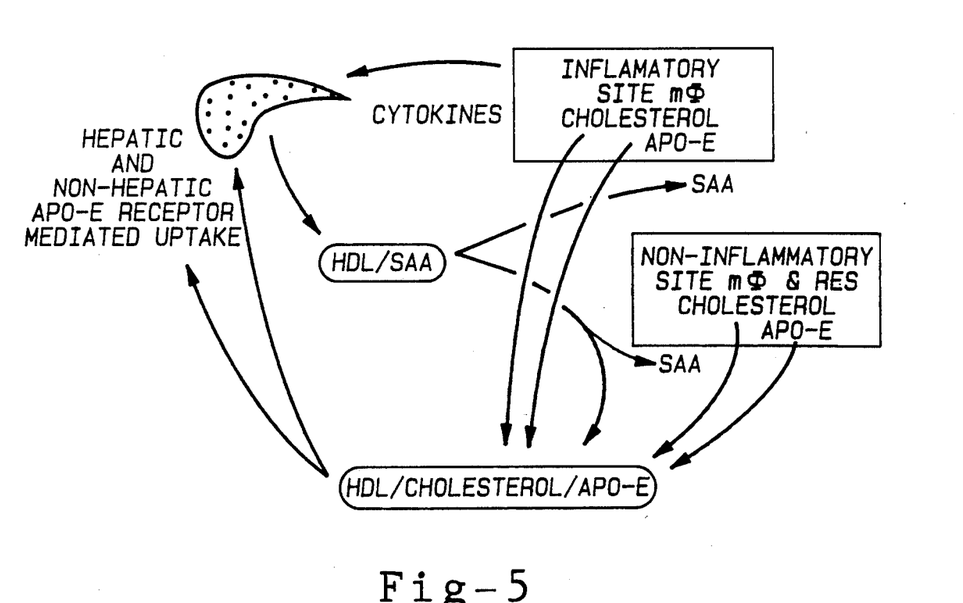
FIG. 5 is a schematic representation of HDL function during inflammatory states.

In an inflammatory reaction cytokines liberated by activated inflammatory cells serve as signals to a variety of cells and organs. In the case of the liver, IL-1, IL-6 and tumor necrosis factor induce the expression of acute phase proteins, among them SAA. SAA in turn associate with HDL as shown herein serves to preferentially direct HDL to macrophages and probably other reticuloendothelial cells (RES). This process would not necessarily depend on the appearance of a new SAA receptor on these cells, although such an event is not excluded. The receptor might already exist on these cells. Its ligand, SAA, would appear only when necessary, addressing HDL to such cells at the time of greatest need, i.e., inflammation. This would be the afferent arm of the reverse cholesterol transport system directing HDL preferentially to those cells which are able to engulf cholesterol and lipid debris, namely macrophage and RES cells. Upon HDL/SAA's interaction with such cells cholesterol afflux and apoE secretion is probably enhanced, a process which has already been demonstrated with macrophages exposed to $HDL_3$, the subfraction to which most of SAA is bound (18,19,20,21). The reverse cholesterol transport arm involving apoE described by others (18,21) would now ensure the redistribution of cholesterol or its excretion. During this process, SAA is probably displaced and released near RES cells and would therefore become available for amyloid formation at these anatomic sites. The entire process is illustrated schematically in FIG. 5. It is one that ensures an efficient and directed lipid/-cholesterol transport mechanism during inflammation. Further, from this postulated role emerges the physiologic reason for the specific anatomic localization of inflammation-type amyloidosis.

In response to cytokines released by activated inflammatory cells, SAA is secreted by the liver, and binds to HDL, primarily $HDL_3$. The HDL/SAA particle has a higher affinity for reticuloendothelial cells such as macrophages, than does HDL alone. In addition, macrophages during inflammation develop increased numbers of binding sites for HDL/SAA. Conversely, hepatocytes lose binding sites for HDL/SAA. A net shift of reverse cholesterol carrying capacity towards macrophage-type cells thus occurs during inflammation. On arrival of HDL/SAA, these cells release apoE and cholesterol, a process which likely displaces the SAA. As demonstrated by others, the HDL/apoE/cholesterol complex is transported to sites for receptor mediated uptake/use or excretion.

The above experimental evidence demonstrates the significant shift in HDL cholesterol carrying capacity towards macrophage. Hence, HDL/SAA provide a relevant and significant therapeutic mechanism for removing cholesterol from macrophages at atherosclerotic sites.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

REFERENCES

1. Hoffman, J. S., Ericsson, L. H., Eriksen, N., Walsh, K. A. & Benditt, E. P. Murine Tissue Amyloid Protein AA: NH2-Terminal Sequence Identity With Only One of Two Serum Amyloid Protein (Apo-SAA) Gene Products. J. Exp. Med. 159:641, 1984.
2. Parmelee, D. C., Titani, K., Ericsson, L. H., Eriksen, N., Benditt, E. P., Walsh, K. A. Amino Acid Sequence of Amyloid-Related Apoprotein (ApoSAA1) From Human High-Density Lipoprotein. Biochem. 21:3298, 1982.
3. Lowell, C. A., Potter, D. A., Stearman, R. S., Morow, J. F. Structure of the Murine Serum Amyloid A Gene Family. Gene Conversion. J. Biol. Chem. 261:8442, 1986.
4. Selinger, M. J., McAdam, KPWJ, Kaplan, M. M., Sipe, J. D., Vogel, S. N., Rosenstreich, D. L. Monokine-induced Synthesis of Serum Amyloid A Protein by Hepatocytes. Nature 285:498, 1980.
5. Ganapathi, M. K., Schultz, D., Mackiewicz, A., Samols, D., Hu, S. I.,, Brabenec, A., MacIntyre, S. S., Kushner, I. Heterogeneous Nature of the Acute Phase Response: Differential Regulation of Human Serum Amyloid A, C-reactive Protein and Other Acute Phase Proteins by Cytokines in Hep 3B Cells. J. Immunol. 141:564, 1988.
6. Steinmetz, A., Hocke, G., Saile, R., Puchois, P., Fruchart, J. C. Influence of Serum Amyloid-A on Cholesterol Esterification in Human Plasma. Biochem, Biophys. Acta. 1006:173, 1989.
7. Glomset, J. A. The Plasma Lecithin: Cholesterol Acyltransferase Reaction. J. Lipid Res. 9:155, 1968.
8. Kisilevsky, R., Axelrad, M. A., Corbett, W. E. N., Brunet, S., Scott, F. The Role of Inflammatory Cells in the Pathogenesis of Amyloidosis. Lab Invest. 37:544, 1977.
9. Schumaker, V. N. Puppione, D. L., Sequential Flotation Ultracentrifugation. Meth. Enzymol. 128:155, 1986.
10. Subrahmanyan, L., Kisilevsky, R. Effects of Culture Substrates and Normal Hepatic Sinusoidal Cells on In Vitro Hepatocyte Synthesis of apo-SAA. Scand. J. Immunol. 27:251, 1988.
11. Lowry, O. H., Rosebrough, N. J., Farr, A. L. Randall, R. J. Protein Measurement With the Folin Phenol Reagent. J. Biol. Chem. 193:265, 1951.
12. Narindrasorasak, S., Lowery, D., Gonzalez-DeWhitt, P., Poorman, R. A., Greenberg, B., Kisilevsky, R. High Affinity Interactions Between the Alzheimer's beta-Amyloid Precursor Proteins amd the Basement Membrane Form of Heparan Sulfate Proteoglycan. J. Biol. Chem. 266:12878, 1991.
13. Brissette, L., Young, I. Narindrasorasak, S., Kisilevsky, R., Deeley, R. Differential Induction of the Serum Amyloid-A Gene Family in Response to an Inflammatory Agent and to Amyloid-Enhancing Factor. J. Biol. Chem. 264:19327, 1989.
14. Miura, K., Baba, S., Shirasawa, H., Ju, S. T., Cohen, A. S., Shirahama, T. Intraperitoneal Amylod Formation by Amyloid Enhancing Factor Rich Macrophages in Ascitic Fluid. In: Amyloid and Amyloidosis 1990, edited by Natvig, J. B., Forre, O., Husby, G., Husebekk, A., Skogen, B., Sletten, K., Westermark, P., p. 523. Dordrecht, Kluwer Academic Publishers, 1991.
15. Fidge, N. H. Nestel, P. J. Identification of Apolipoproteins Involved in the Interaction of High Density Lipoprotein3 With Receptors on Cultured Cells. J. Biol. Chem. 260:3570, 1985.
16. Schmitz, G., Robenek, H., Lohmann, U., Assmann, G. Interaction of High Density Lipoproteins With Cholesteryl Ester Laden Macrophages: Biochemical and Morphological Characterization of Cell Surface Receptor Binding, Endocytosis, and Resecretion of High Density Lipoproteins by Macrophages. EMBO J. 4:613, 1985.
17. van der Westhuyzen, D. R., Coetzee, G. A., de Beer, F. C. Serum Amyloid A Protein in Plasma: Characteristics of Acute Phase HDL. In: Amyloidosis, edited by Marrink, J., Van Rijswijk, M. H., p. 115, Martinus, Nijhoff, Dordrecht, 1986.
18. Basu, S. K., Ho, Y. K., Brown, M. S., Bilheimer, D. W., Anderson, R. G. W., Goldstein, J. L. Biochemical and Genetic Studies of the Apoprotein E Secreted by Mouse Macrophages and Human Monocytes. J. Biol. Chem. 257:9788, 1982.
19. Dory, L. Regulation of Apolipoprotein-E Secretion by High Density Lipoprotein3 in Mouse Macrophages. J. Lipid. Res. 32:783, 1991.
20. Hara, H., Yokoyama, S. Interaction of Free Apolipoproteins With Macrophages—Formation of High Density Lipoprotein-Like Lipoproteins and reduction of Cellular Cholesterol. J. Biol. Chem. 266:3080, 1991.
21. Mahley, R. W. Apolipoprotein E: Cholesterol Transport Protein With Expanding Role in Cell Biology. Science 240:622, 1988.

What is claimed is:

1. A method of potentiating the release and collection of macrophage cholesterol in vivo comprising:
   administering an effective amount of high-density lipoprotein (HDL) bound to a ligand having serum amyloid A (SAA) affinity for HDL which potentiates the affinity of HDL for macrophages, thereby exposing macrophages to the HDL bound to the ligand; and potentiating macrophage cholesterol release for subsequent macrophage cholesterol excretion.

2. A method as claimed in claim 1 wherein said ligand having SAA affinity for HDL is serum amyloid A and said exposing step is further defined as exposing the macrophage to an amount of SAA bound to HDL effective to increase macrophage cholesterol release for subsequent macrophage cholesterol excretion.

3. A method as claimed in claim 2 wherein said potentiating step is further defined as increasing the amount and affinity of binding sites for HDL on macrophages.

4. A method as claimed in claim 3 further defined as decreasing the amount and affinity of binding sites for HDL on hepatocytes.

* * * * *